United States Patent [19]

Matson

[11] Patent Number: 4,795,704
[45] Date of Patent: Jan. 3, 1989

[54] MULTIPHASE ASYMMETRIC MEMBRANE REACTOR SYSTEMS

[75] Inventor: Stephen L. Matson, Harvard, Mass.

[73] Assignee: Sepracor, Inc., Marlborough, Mass.

[21] Appl. No.: 786,764

[22] Filed: Oct. 11, 1985

[51] Int. Cl.[4] .................. C12P 1/00; C12N 11/08; C12N 11/04; C12M 1/40
[52] U.S. Cl. ..................... 435/41; 435/179; 435/180; 435/182; 435/288
[58] Field of Search ............... 435/41, 174, 177, 179, 435/180, 182, 288

[56] References Cited

U.S. PATENT DOCUMENTS

| | | | |
|---|---|---|---|
| 4,266,026 | 5/1981 | Breslau | 435/182 X |
| 4,415,666 | 11/1983 | Orazio et al. | 435/182 X |
| 4,418,148 | 11/1983 | Oberhardt | 435/182 X |
| 4,440,853 | 4/1984 | Michaels et al. | 435/182 X |

FOREIGN PATENT DOCUMENTS 0068594 1/1983 European Pat. Off. ............ 435/182

*Primary Examiner*—David M. Naff
*Attorney, Agent, or Firm*—Pennie & Edmonds

[57] ABSTRACT

A catalyst such as an enzyme is contained in an asymmetric membrane between two immiscible liquid streams. A catalytic reaction is carried out by introducing a reactant to one stream and removing a product from the other stream. When the catalyst becomes deactivated, the membrane can be recharged with catalyst by displacing the deactivated catalyst and introducing fresh catalyst. The membrane has a skin layer that has pores sufficiently small so as to prevent leakage of the catalyst and a highly porous region that contains the catalyst. Insolubility of the catalyst in the immiscible liquid prevents loss of the catalyst for the highly porous region.

5 Claims, 4 Drawing Sheets

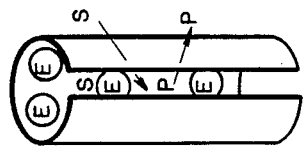
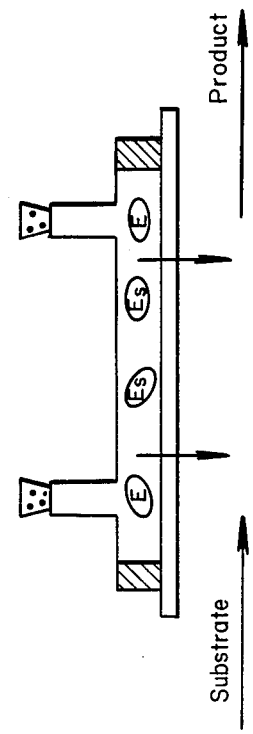
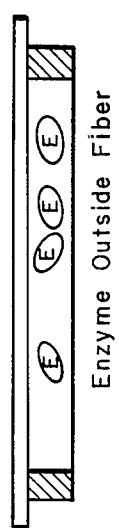
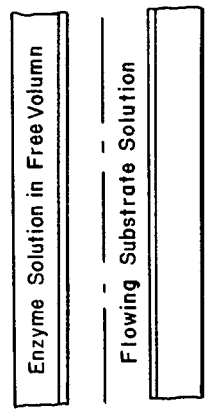
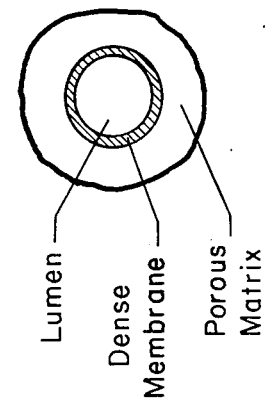

MULTIPHASE ASYMMETRIC MEMBRANE REACTOR SYSTEMS

TECHNICAL FIELD

The present invention relates to novel apparatus in which enzymes and other catalysts are confined within membranes for use as membrane reactors in multiphase reaction systems. The invention also relates to a variety of membranes having different solvent-wetting character and configurations, and to methods for charging such membranes with catalysts and for regenerating the membrane reactors once the catalysts therein confined have become inactivated through use.

BACKGROUND OF THE INVENTION

A method and apparatus are disclosed for the confinement or containment of a catalyst either in an asymmetric membrane or in a composite membrane structure, which is subsequently used to conduct a chemical or biochemical reaction in which multiple phases (e.g. organic and aqueous) are involved.

"Immobilization" on solid-phase supports of otherwise homogeneous catalysts (including, but not limited to enzymes, whole cells, and non-biological catalysts such as various metal-containing coordination compounds) is useful because immobilization simplifies the separation of reaction products from catalyst and it facilitates the recovery and reuse of catalyst, which frequently is too expensive for one-time use. However, as discussed below, such catalyst immobilization is often accomplished by covalently attaching the catalyst to the support, generally via irreversible, covalent linking chemistry. As a result, when a supported catalyst becomes deactivated, as biocatalysts such as enzymes inevitably do, it is difficult if not impossible to replace the catalyst without at the same time replacing the support matrix. Replacement of the catalyst/support combination can be a considerably more expensive proposition than replacement of the catalyst component alone because of the cost of the immobilization chemistry and of the support itself.

Typical supports are membrane structures and particulate media such as microporous and gel-type beads. Membrane supports are attractive because membrane reactors have a number of performance advantages relative to packed-bed reactors employing catalysts bound to particulate support media. However, they have the significant disadvantage that membrane supports are expensive relative to particulate media. Accordingly, the costs associated with periodically replacing membrane-supported catalysts can be significantly higher than is the case with particulate supports.

A significant improvement in membrane bioreactor economics would result from the localization of catalysts in a membrane structure in such a way as to (1) provide effective containment of the catalyst in the membrane, (2) permit high effective catalyst loadings to be realized, and (3) make possible simple catalyst replacement by avoiding the covalent attachment of catalyst to the membrane surface. Such a technology would significantly reduce the cost of catalyst replacement in membrane reactors. Additionally, it could have secondary benefits of avoiding the use of immobilization chemistries that can be expensive and difficult to control and that sometimes can result in disappointing yields and/or activities of immobilized catalyst.

Many approaches exist for the immobilization of enzymes and homogeneous catalysts on solid supports. Several techniques including covalent bonding, crosslinking, entrapment, adsorption, and microencapsulation have been developed to render many enzymes water-insoluble. See FIG. 1A. Reviews of enzyme immobilization procedures have been published. Zaborsky, O. R., *Immobilized Enzymes*, CRC Press, Cleveland, Ohio (1973); Weetal, H. H., ed., *Immobilized Enzymes, Antigens, Antibodies, and Peptides: Enzymology*, Vol. 1, Marcel Dekker, N.Y. (1975); Gutcho, S. J., *Immobilized Enzymes—Preparation and Engineering Techniques*, Noyes Data Corp., Park Ridge, N.H. (1974). Several industrial processes currently employ immobilized enzymes or immobilized whole cells. Mosbach, K., "Application of Immobilized Enzymes," pp. 717-858 in *Immobilized Enzymes*, K. Mosbach, ed., *Methods in Enzymology XLIV*. Academic Press, N.Y. (1976).

The possibility of immobilizing non-biological, ionic homogeneous catalysts as the counterions in ion exchange resins has been recognized for over thirty years. Helfferich, F., *Ion Exchange*, McGraw-Hill, N.Y. (1971). More recently, homogeneous catalyst complexes have been tied to polymeric and ceramic supports via bifunctional ligands which are simultaneously coordinated with the active metal center and anchored to the solid support. Pittman, C. U., and Evans, G. O. *Chemtech*, 3, 560 (1975); Michalska, Z. M., and Webster, D. E., *Chemtech*, 5, 117 (1975); Grubbs, R. H., *Chemtech*, 7, 512 (1977); Bailar, J. C., Jr., *Cat. Rev.—Sci. Eng.*, 10(1), 17 (1974). Examples are shown in FIGS. 1B and 1C.

Enzymes have been immobilized in membranes (as opposed to particles) in several different fashions. They have been covalently bound or crosslinked within porous membranes (Thomas, D., "Artificial enzyme membranes: transport, memory, and oscillatory phenomena," pp. 115-150 in *Analysis and Control of Immobilized Enzyme Systems*, D. Thomas and J. P. Kernevez, eds., American Elsevier, N.Y. (1976); Thomas, D., and Caplan, S. R., "Enzyme Membranes," pp. 351-398 in *Membrane Separation Processes*, P. Meares, ed., Elsevier, Amsterdam (1976); Fernandes, P. M., Constanides, A., Vieth, W. R., and Vendatasubramanian, K., *Chemtech*, 5, 438 (1975); Goldman, R., Kedem, O., and Katchalski, E., *Biochem*, 7, 4518 (1968)), attached to membrane surfaces (Emery, A., Sorenson, J., Kolarik, M., Swanson, S., and Lim, H., *Biotechnol. Bioeng.*, 16, 1359 (1974)), entrapped in membrane gels (Blaedel, W. J., Kissel, T. R., and Bogulaski, R. C. *Anal. Chem.*, 44, 2030 (1972); Blaedel, W. J., and Kissel, T. R., *Anal. Chem.*, 47, 1602 (1975)), encapsulated by polymeric or liquid surfactant membrane microcapsules, (Chang, T. M. S., *Artificial Cells*, Charles C. Thomas, Springfield, Ill. (1972); Chang, T. M. S., and Kuntarian, N., pp. 193-197 in *Enzyme Engineering* 4, G. B. Brown, G. Manecke, and L. B. Wingard, eds., Plenum Press, N.Y. (1978); May, S. W., and Landgraff, L. M., *Biochem. Biophys. Res. Commun.*, 68,786 (1976); Mohan, R. R., and Li, N. N., *Biotechnol. Bioeng.*, 16, 513 (1974).) and confined to reaction vessels by ultrafiltration membranes (Porter, M. C., "Applications of Membranes to Enzyme Isolation and Purification," pp. 115-144 in *Enzyme Engineering* 3, L. B. Wingard, ed., Interscience, N.Y. (1972); Closset, G. P., Cobb, J. T., and Shah, Y. T., *Biotechnol. Bioeng.*, 16, 345 (1974); Madgavkar, A. M., Shah, Y. T., and Cobb, J. T., *Biotechnol. Bioeng.*, 19, 1719 (1977)). The latter type of containment with membranes has been called "figurative immobilization" by Weetal (Messing, R. A., ed., *Immobilized Enzymes for Industrial Reactors*, Academic Press, N.Y. (1975)), a term which also applies to the localization of an enzyme solution by hollow fibers (Rony, P. R., *J. Am. Chem. Soc.*, 94, 8247 (1972); Davis, J. C., *Biotechnol. Bioeng.*, 16, 1113 (1974); Lewis, W., and Middleman, S., *AIChE J.*, 20, 1012 (1974); Waterland, L. R., Robertson, C. R., and Michaels, A. S., *Chem. Eng. Commun.*, 2, 37 (1975)). Enzyme entrapment outside the fiber (i.e., within the "shell"), within the porous matrix, and in the fiber lumen have all been demonstrated in fully aqueous systems where reactants and products have been supplied and withdrawn, respectively, in aqueous process streams (see FIGS. 2A, 2B, 2C).

Every conceivable membrane geometry—planar films (Kay, T., Lilly, M. D., Sharp, A. K., and Wilson, R. J. H., *Nature*, 217, 641 (1968); Wilson, R. J. H., Kay, G., and Lilly, M. D., *Biochem. J.*, 108, 845 (1968a); Wilson, R. J. H., Kay, G., and Lilly, M. D., *Biochem. J.*, 109,137 (1968b)) and spiral-wrapped membranes (Vieth, W. R., Wang, S. S., Bernath, F. R., and Mogensen, A. O., "Enzyme Polymer Membrane Systems," pp. 175–202 in *Recent Developments in Separation Science*, Vol. 1, N. N. Li, ed., CRC Press, Cleveland, Ohio (1972); Broun, G., Thomas, D., Gellf, G., Domurado, D., Berjonneau, A. M., and Buillon, C., *Biotechnol. Bioeng.*, 15, 359 (1973); Gautheron, D. C., and Coulet, P. R., pp. 123–127 in *Enzyme Engineering* 4, G. B. Broun, G. Manecke, and L. B. Wingard, eds., Plenum Press, N.Y. (1978)), tubular membranes, (Madgavkar, A. M. Shah, Y. T., and Cobb, J. T., *Biotechnol. Bioeng.*, 19, 1719 (1977); Tachauer, E., Cobb, J. T., and Shah, Y. T., *Biotechnol. Bioeng.*, 16, 545 (1974)) and hollow fibers and microcapsules—and nearly all membrane types—porous and nonporous, electrically charged and neutral—have been considered in connection with enzyme immobilization.

SUMMARY OF THE INVENTION

Briefly stated, the present invention operates by trapping a catalyst between two catalyst-impermeable boundaries that it cannot cross under normal membrane reactor operating conditions. These two barriers to catalyst transport are, generally speaking, (1) a "skin" or surface layer of said support membrane structure, which contains pores that are sufficiently small so as to prevent the transport and leakage of catalyst (which will often be either macromolecular or particulate in nature), and (2) a liquid-liquid phase boundary (e.g., between an aqueous solution entrapped in the pores of the membrane and an organic solvent residing just outside of it) that is located at the opposite surface of the catalyst-containing membrane structure. On one surface of the membrane structure, the size of the catalytic species prevents it from diffusing across the skin or surface layer of the asymmetric or composite membrane, while on the other surface the poor solubility of the catalyst in the immiscible liquid phase residing just outside of the membrane prevents loss of the catalytic species from that surface.

As an example, water-soluble enzymes used in two-phase and/or extractive membrane bioreactors could readily be contained in asymmetric, ultrafiltration-type membranes prepared from suitably hydrophilic polymers, where the membrane skin and the aqueous/organic phase boundary at opposite surfaces of the membrane would serve to confine the biocatalyst to the interior region of the water-wet porous membrane. Alternatively, a two-layer composite structure consisting of a gel-type diffusion membrane (as used, for example, in dialysis) atop a microporous membrane support could also be employed for catalyst containment.

In cases where catalyst lifetime is short compared to that of the membrane support, the present invention makes possible the removal of deactivated catalyst and economical replacement thereof with active catalyst.

Few of the above-cited prior-art immobilization techniques bear much similarity to the present invention, either in structure or in function. Perhaps microencapsulation comes closest to the present invention, involving as it does a selective membrane barrier that prevents loss of catalyst from the interior; generally, selectivity is based on the size of the catalyst relative to the diameter of the pores in the microcapsule wall. However, microcapsules have but a single interface with the process stream (i.e., the microcapsule wall), and as a result the encapsulated catalyst is in contact with only a single process stream. In contrast, it is a purpose of the present invention to immobilize catalysts in membrane structures that permit close contact of the catalyst with multiple (and often immiscible) process streams.

BRIEF DESCRIPTION OF THE FIGURES

The present invention may be more readily understood by reference to the following figures, wherein:

FIGS. 2A, 2B and 2C are schematic representations of some conventional hollow fiber membrane/enzyme reactors as have been investigated for fully aqueous systems, with enzyme outside a fiber in a shell, enzyme in the porous matrix of a fiber, and enzyme in the lumen of a fiber shown in FIGS. 2A, 2B and 2C, respectively;

DETAILED DESCRIPTION OF THE INVENTION

Figure 1A:
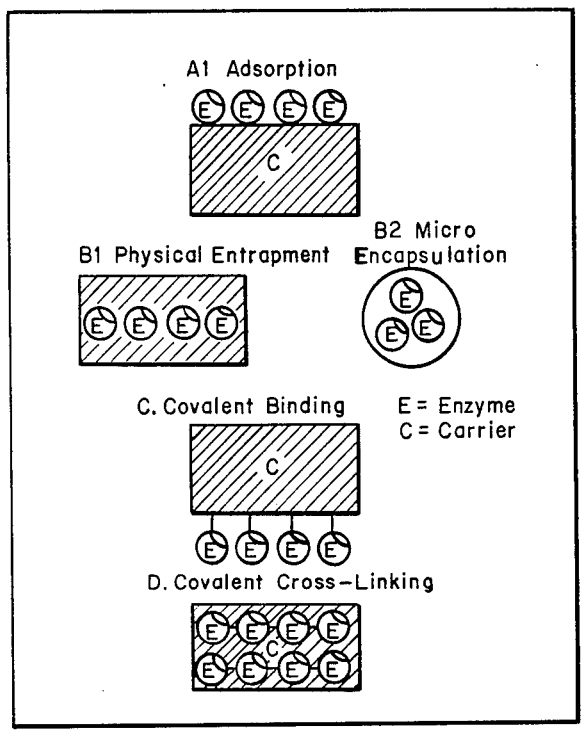
FIGS. 1A, 1B and 1C are schematic representations of commonly used catalyst immobilization techniques, with conventional methods for enzyme and for non-biological catalyst immobilization shown in FIG. 1A and FIGS. 1B and 1C, respectively.
Figure 1B:
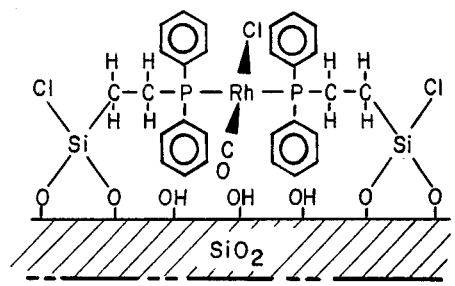
Figure 1C:
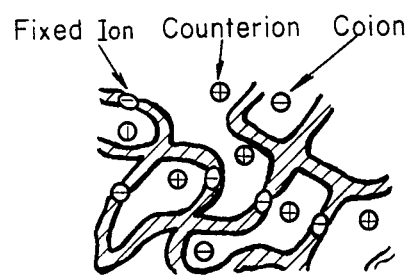
Figure 3:
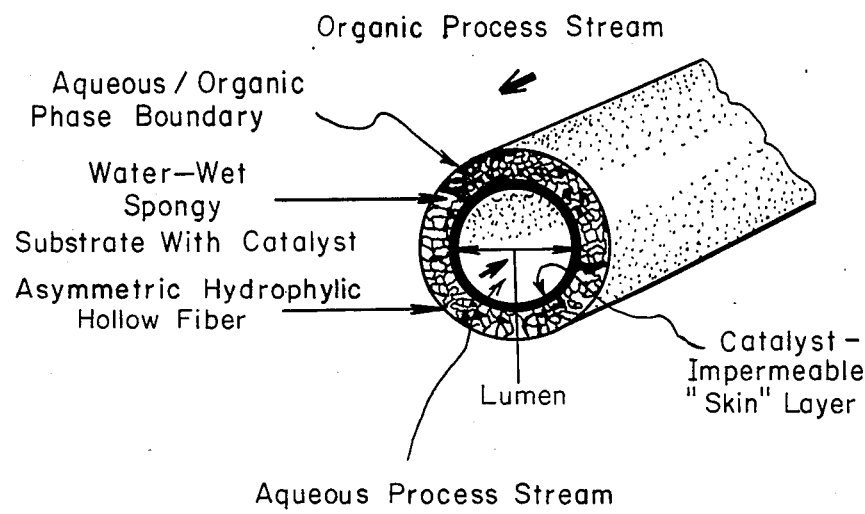
FIG. 3 is a schematic representation of an illustrative embodiment of the invention in which a biocatalyst is contained within an inside-skinned, hydrophilic hollow, fiber.

FIG. 3 shows a preferred embodiment of the present invention based on the use of a single asymmetric membrane with appropriate surface properties and wetting characteristics. Asymmetric membranes suitable for the practice of this invention are chosen from the group of anisotropic ultrafiltration (UF) and microfiltration (MF) membranes. These are characterized by a more-or-less thin "skin" layer, which in the case of UF membranes is on the order of 0.1–0.2 $\mu$m in thickness, supported atop a much thicker (100–200 $\mu$m) and highly porous substrate region. The skin of appropriate asymmetric UF- and MF-type membranes is characterized by sufficiently small pores (10's of Angstroms to perhaps 100 Angstroms in diameter) that macromolecular catalysts such as enzymes and colloidal or particulate catalysts are prevented from diffusing across to be lost to a process stream. Thus, the skin or surface region of the asymmetric membrane forms one catalyst-impermeable boundary.

The required characteristics of the "skin" layer will, of course, depend strongly on the size and other properties of the catalyst that is to be retained. In addition to the ultraporous (or even finely microporous) skin structures contemplated in the above paragraph, it may be advantageous in other situations to employ asymmetric membrane structures characterized by surface layers that resemble swollen gel-type membranes such as the type used in dialysis, or even to employ relatively "tight" membrane materials such as those used in thin-film-composite reverse osmosis membranes (generally for non-biologically catalyzed reactions).

The pores in the highly porous substrate region underlying the "skin" region of the membrane support can be and preferably are much larger (0.02 $\mu$m to several $\mu$m's in diameter) than those in the skin. The diameter of these substrate pores is chosen with two constraints in mind: (1) the pores must be large enough to accommodate the catalyst, which, in the case of whole cells, may be several microns in diameter and (2) the pores must be sufficiently small (a few microns at most) that capillary forces within them are significant. The latter consideration is important because the porous membrane substructure must be "wet" or impregnated by the "correct" liquid phase (e.g., usually the aqueous phase in the case of an enzyme-catalyzed conversion), and hence it is important that the intrusion pressure (the pressure at which the "incorrect" fluid can be forced into the pores of the substrate) not be exceeded during operation of the reactor. The intrusion pressure $\Delta P$ is inversely related to pore radius $r_{pore}$ by the Young-LaPlace equation:

$$\Delta P = (2\gamma/r_{pore})\cos \theta \quad (1)$$

where $\gamma$ is the interfacial tension between the organic and aqueous phases and $\theta$ is the contact angle between the membrane material and the liquid phase contained therein. Typically, substrate pore sizes will be chosen such that the intrusion pressure is at least several psi, to ensure stable operation of the membrane-contained catalyst.

The second catalyst-impermeable boundary that defines the catalyst-containing region is defined by the liquid-liquid interface (typically, an aqueous/organic phase boundary) that is located at the surface of the membrane furthest removed from the "skin" layer. Capillarity acts to confine the desired liquid phase to the highly porous membrane matrix, and to exclude the other, immiscible liquid phase. Shown in FIG. 3 is the situation wherein the catalyst is water-soluble or hydrophilic (i.e., preferentially wet by water), and the membrane material is chosen also to be hydrophilic. In this case, the aqueous/organic phase boundary will reside essentially at the outer, unskinned surface of the membrane, assuming that the pressure difference across the membrane is not in the direction so as to cause ultrafiltration of aqueous solution across the membrane or not so large as to cause intrusion of organic solvent into it. Under these circumstances, a water-soluble or hydrophilic catalyst will be confined to the aqueous interior of the membrane by virtue of its inability to partition into the organic solvent phase and subsequently be carried out of the reactor with it.

It is recognized that the relatively thick microporous substrate region that underlies the relatively thin skin layer of integrally skinned asymmetric membranes will often contain so-called macrovoids or "fingers" that are characterized by dimensions an order of magnitude or more larger than the diameter of the more prevalent micropores comprising the bulk of the substrate. Such macrovoid-containing asymmetric membranes are also within the scope of the present invention. For instance, for the particular case where the membrane is hydrophilic in nature, it is contemplated that the small micropores will be filled with aqueous catalyst-containing solution—retained in the micropores by capillary action—while the much larger macrovoids extending through the substrate will be filled with organic solvent. Intrusion of organic solvent into the macrovoids can be made to occur by applying a small amount of positive pressure to the organic phase sufficient to overcome the relatively small intrusion pressure associated with the larger diameter macrovoids (see Equation 1). In this manner, the area of aqueous/organic interface can be made larger than the superficial geometric area of the outer envelope of the membrane. For purposes of this disclosure, such area of the membrane where the aqueous/organic interface is located will be refered to as one of the surfaces of the membrane. Hydrophobic asymmetric membranes containing macrovoids can be employed for the containment of organic-soluble catalyst in the microporous region of the substrate, the macrovoid being filled with aqueous solution in this case.

Several variations on this general theme can be identified. For example, the geometry of the asymmetric membrane is largely irrelevant to the present invention, whether the membrane be in the form of flat sheets, tubes, or hollow fibers (although the latter will usually be preferred from the points of view of manufacturability and cost). Moreover, both inside-skinned (as shown in FIG. 3) and outside-skinned hollow fibers, sheets or tubes may be employed, and the membrane material may be either hydrophilic (i.e., water-wet) or hydrophobic (i.e., preferentially wet by organic solvents). Considering just these two dimensions of skin location (i.e., inside- vs. outside-skinned) and surface properties (i.e., hydrophobic vs. hydrophilic), it is apparent that four different configurations can be identified, each of which will have its own set of advantages, disadvantages, and potential applications:

inside-skinned, hydrophilic,
inside-skinned, hydrophobic,
outside-skinned, hydrophilic, and
outside-skinned, hydrophobic.

Figure 4:
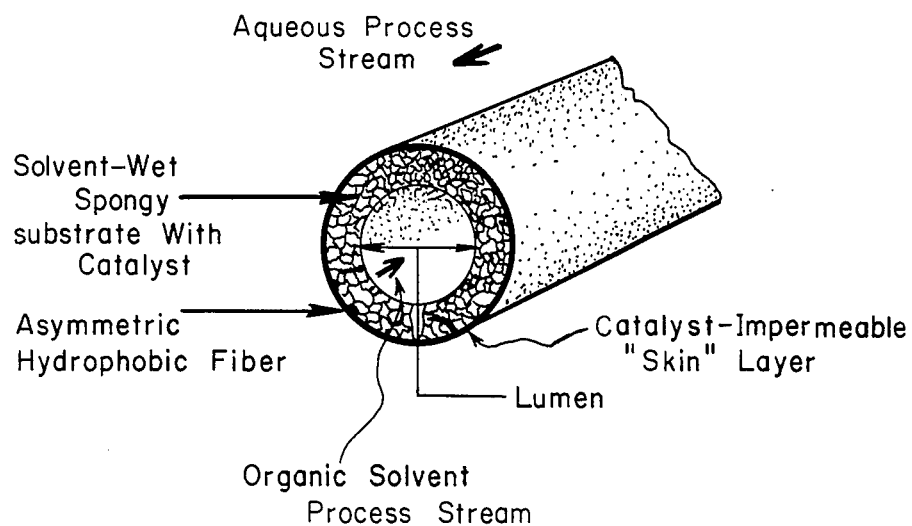
FIG. 4 is a schematic representation of an illustrative embodiment of the invention in which a non-biological homogeneous catalyst is contained within an outside-skinned, hydrophobic hollow fiber.

For example, the outside-skinned and hydrophobic hollow-fiber of FIG. 4 may have utility in the conduct of phase-transfer catalyzed reactions, where the catalytic species is present predominantly in the organic phase. (In this case, a macromolecular tail on the catalyst would assist in retaining it in the membrane matrix.)

The present invention can be further categorized according to the nature of the catalysts and reactions involved. For example, the present invention is useful both for localizing enzymes that are dissolved in the aqueous phase, as well as those that operate at aqueous/organic phase boundaries, such as certain of the lipases. Moreover, despite the focus of the above discussion, it is important to note that the utility of the invention is not limited to "bioconversions" such as those catalyzed by enzymes and viable or non-living whole cells. Various catalytic reactions of synthetic organic chemistry involve multiple phases (e.g., phase-transfer catalyzed reactions), and the present invention is equally useful in these cases. Finally, both soluble (typically, macromolecular) and particulate catalysts can be localized according to the method of the present invention.

The membrane structure of the present invention is operated in a diffusive mode, i.e., with diffusive transport of reactants into and products out of the catalytic region of the membrane; convective flow through the membrane is to be avoided. Preferably, reactants diffuse in on one side of the structure, and products diffuse out on the other, so that a separation and/or purification is accomplished simultaneously with the catalytic conversion.

The present invention is particularly useful in the conduct of catalyzed reactions in "multiphase" or "extractive" membrane reactors, where two process streams—one aqueous and one organic—are located on opposite surfaces of the catalyst-containing membrane and serve the purpose of supplying reactant or removing product. For example, in cases where a reactant is soluble in organic solvents but not in water and where the reaction product is water soluble, the reactant may be fed to the reactor via a stream of organic solution directed past one surface of the membrane of the present invention, while the water-soluble product may be withdrawn from the opposite surface of the membrane via a second, aqueous process stream. In other cases, a water-soluble reactant may be supplied via an aqueous stream directed past one surface of the membrane of the present invention while the product is made to partition and is thereby removed into a stream of organic solvent flowing past the other surface of the membrane.

The manner of loading the membrane with catalyst is illustrated here for the case of an enzymatic reaction conducted in the hydrophilic and inside-skinned hollow-fiber membrane of FIG. 3. Initially, aqueous enzyme solution is charged to the shell (or outer) side of the hollow-fiber module and passed though the fiber wall in an ultrafiltration process under a modest pressure difference (i.e., a pressure insufficient to cause disruption or loss of integrity of the skin under "backflush" conditions). During this step, enzyme is accumulated in the porous substrate region of the fiber. Next, excess aqueous enzyme solution is displaced from the shell side of the fiber bundle by flushing it with an immiscible fluid such as air or the organic process solvent. If air or another gas is used in this step, the shell is filled with the organic solvent in a subsequent step. The module is then operated with the organic solvent on the shell side and an aqueous solution in the lumen of the fiber with a slight excess pressure on the shell side. This pressure difference is too small to cause intrusion of the organic phase into the substrate region of the fiber on the one hand and is in the wrong direction to cause ultrafiltration of aqueous solution on the other hand.

When the enzyme becomes deactivated and must be recharged, a positive pressure is applied to the aqueous solution on the interior or lumen side of the fibers, thereby causing ultrafiltration (i.e., convective flow) through the membrane and displacement both of organic solvent from the shell side of the module as well as deactivated enzyme from the fiber walls. In order to reload the membrane with catalyst, the steps of the preceding paragraph are repeated.

Figure 5:
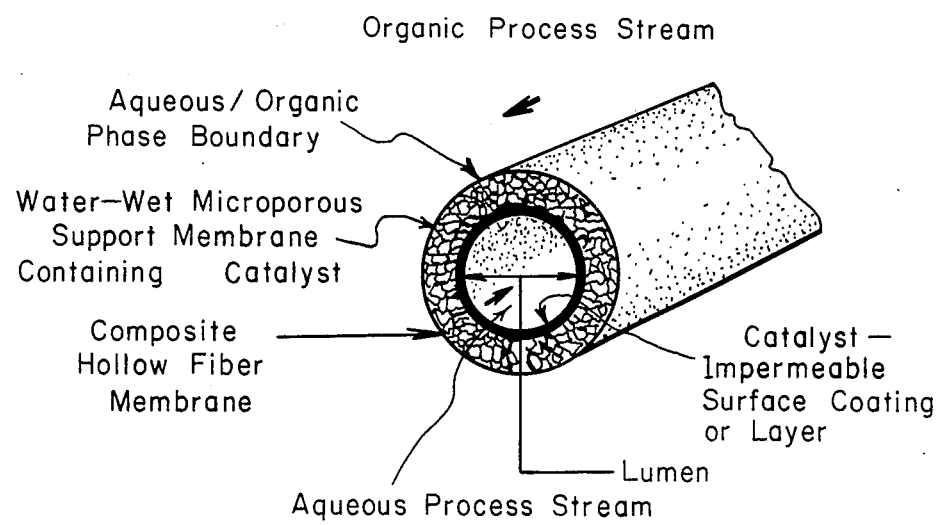
FIG. 5 is a schematic representation of an illustrative embodiment of the invention in which a biocatalyst is contained within a composite, hydrophilic hollow fiber.

In another embodiment, a composite membrane structure is employed in place of the asymmetric, integrally skinned membranes contemplated above. As shown in FIG. 5, this composite consists of a thin, permselective surface layer of one material supported on a highly porous and much thicker nonselective substrate membrane, generally fashioned from a different material. Techniques for the fabrication of multilayer composite, laminated and coated membrane structures are well known in the art and are the subject of published review articles. Matson, S. L., Lopez, J. and J. A. Quinn, *Chem. Eng. Sci.*, 38, 503 (1983); Lonsdale, H. K., *J. Memb. Sci.*, 10, 81, (1982).

For example, composite membrane structures suitable for the localization of various biocatalysts might be manufactured based on the use of thin surface coatings of regenerated cellulose dialysis-type membrane supported on microporous membranes, particularly microporous hollow fibers. Alternatively, a suitably microporous layer might be deposited upon or within a regenerated cellulose hollow fiber. Hydrophilic polyacrylonitrile-based copolymer membranes also appear to be well suited to construction of such types of composite membrane structures.

What is claimed is:

1. A method for containing a catlayst within an asymmetric membrane between two immiscible liquid streams comprising:
   (a) Providing an asymmetric membrane having
      (i) a first surface having a skin having pores that are large enough to allow permeation by reactants or products but small enough to substantially prevent catalyst leakage; and
      (ii) a second surface having pores that are large enough to allow permeation by reactants, products and catalyst;
   (b) charging a catalyst into said asymmetric membrane by adding said catalyst to a first liquid stream and contacting the second surface of said asymmetric membrane with said first liquid stream containing said catalyst, said first liquid stream wetting said asymmetric membrane and thereby providing said catalyst and said first liquid stream into said asymmetric membrane;
   (c) proviidng said first liquid stream without said catalyst to the first surface of said asymmetric membrane;
   (d) replacing said first liquid stream containing said catalyst used in charging said asymmetric membrane at the second surface with a second liquid stream in which said catalyst is not appreciably soluble, which second liquid stream is substantially immiscible with said first liquid stream present at said first surface of said asymmetric membrane; and
   (e) providing said second liquid stream under a greater pressure than said first liquid stream so as to maintain a interface between said first and second liquid streams at said second surface
thereby containing said catalyst within said asymmetric membrane between said first and second liquid streams which are immiscible.

2. The method of claim 1 wherein, after step (e), introducing a reactant to one of said first and second liquid streams and removing a product from the stream to which the reactant is not introduced.

3. The method of claim 2 wherein, when said catalyst becomes deactivated, displacing said catalyst from said asymmetric membrane by applying a positive pressure to said first surface and charging fresh catalyst into said asymmetric membrane by repeating steps (b)–(e).

4. The method of claim 2 wherein said reactant is introduced to the first liquid stream and said product is removed in the second liquid stream.

5. The method of claim 2 wherein said reactant is introduced to the second liquid stream and said product is removed in the first liquid stream.

* * * * *